United States Patent [19]

Wimberley

[11] 4,067,693

[45] Jan. 10, 1978

[54] METHOD FOR GEOCHEMICAL PROSPECTING

[75] Inventor: Jerry W. Wimberley, Ponca City, Okla.

[73] Assignee: Continental Oil Company, Ponca City, Okla.

[21] Appl. No.: 506,361

[22] Filed: Sept. 16, 1974

[51] Int. Cl.² ............................................. G01N 33/24
[52] U.S. Cl. ................................................. 23/230 EP
[58] Field of Search ................................... 23/230 EP

[56] References Cited

U.S. PATENT DOCUMENTS

| | | | |
|---|---|---|---|
| 2,348,103 | 5/1944 | Beckman | 23/230 EP |
| 3,434,800 | 3/1969 | Ward | 23/230 EP |
| 3,730,683 | 5/1973 | Milly | 23/230 EP |

*Primary Examiner*—Robert M. Reese
*Attorney, Agent, or Firm*—F. Lindsey Scott

[57] ABSTRACT

A method for locating subterranean sulfide mineral ore deposits by analyzing the soil at a plurality of locations in an area of interest to determine the ratio between mercury present in the soil as mercury sulfide and the total mercury present in the soil and, thereafter, comparing the ratios to determine the location of sulfide mineral ore deposits.

5 Claims, No Drawings

METHOD FOR GEOCHEMICAL PROSPECTING

This invention relates to methods for geochemical prospecting.

This invention further relates to a method for locating subterranean sulfide mineral ore deposits.

This invention more particularly relates to a method for locating subterranean sulfide mineral ore deposits by analyzing the soil at a plurality of locations in an area of interest to determine the ratio between mercury present in the soil as mercury sulfide and the total mercury present in the soil.

As a result of the high demand for metals for use in industry and the like, there has long been a considerable interest in improved methods for locating mineral ore deposits. Many commonly used metals, such as copper, zinc, lead, silver, cadmium, mercury, and the like, frequently occur as sulfide ores in subterranean deposits. Numerous methods have been used in attempts to locate such mineral deposits. Most such methods require extensive drilling, coring, and the like to determine the presence of subterranean mineral ore deposits. Other methods are available, such as shown in U.S. Pat. No. 3,730,683, issued May 1, 1973, to Milly, for determining the general vicinity of subterranean mineral deposits. Other methods for locating subterranean mineral deposits include seismic prospecting, drilling, coring, and the like.

Clearly, such methods leave much to be desired, since they are cumbersome and involve expensive testing techniques. Accordingly, a continuing search has been directed to the development of a method which is relatively inexpensive to use and which reliably indicates the presence of subterranean mineral ore deposits.

It has now been found that subterranean sulfide mineral ore deposits are readily located by a method consisting of a. analyzing the soil at a plurality of locations in an area of interest to determine a ratio between mercury present in the soil as mercury sulfide and the total mercury present in the soil at such locations; and b. comparing the ratios to determine the location of sulfide mineral ore deposits in the area of interest.

The present method is useful in locating sulfide mineral ore deposits generally. Commonly occurring sulfide mineral ore deposits are the sulfide ores of metals selected from the group consisting of copper, zinc, lead, silver, cadmium, mercury, mixtures thereof, and the like. Such metals are commonly found as mixtures in varying proportions in naturally occurring sulfide mineral ore deposits.

In the practice of the method of the present invention, soil samples are collected at a plurality of locations distributed over an area of interest. The samples should be representative of the soil at the location. In some instances, it may be desirable to take the soil samples at some distance beneath the soil surface, although it is believed that unless the surface has been contaminated with mercury and the like, it will be unnecessary to take the samples at any substantial distance beneath the surface. In particular, the samples are desirably taken at depths ranging from 2 to 13 inches, although deeper samples could, of course, be used if desired. It has been observed that with samples taken at varying depths at closely adjacent locations, while the total mercury in the samples may vary, the ratio of the mercury sulfide to the total mercury present in the soil in each instance was remarkably constant.

The mercury sulfides are present as $HgS$, $Hg_2S$, and mixtures thereof. Desirable results have been obtained wherein the ratio of $HgS$ to the total mercury present in the soil was used. Of course, the ratio may be expressed in varying ways, such as the ratio of $HgS$ to the total mercury present in the soil, the ratio of $HgS$ to the other forms of mercury present in the soil, and the like. It will be recognized that the ratio of mercury sulfide to total mercury is considered in all such ratios however expressed. The use of different ratios is possible since the primary use of the ratio is for comparative purposes only, as will be shown more fully hereinafter.

The determination of the mercury sulfide and the total mercury present in the soil may be by any accepted laboratory technique. Desirable results have been obtained wherein the soil samples were heated progressively, with the evolved mercury being absorbed in an apparatus similar to that shown in U.S. Pat. No. 3,693,323 issued Sept. 26, 1972, to Preston Gant. The collected mercury is then analyzed. It is known that the various forms of mercury, such as mercury sulfide, mercury oxide, mercury halide, and the like, thermally decompose at different temperatures. It is thus possible to determine the particular form of mercury which has decomposed to yield the mercury collected in the mercury trap at a given temperature. Such calibrations are well known as those skilled in the art and need not be discussed extensively. It is pointed out, however, that such calibrations are readily accomplished by merely heating a soil sample to a temperature such that no further mercury is evolved, thereafter cooling the soil sample and adding a particular form of mercury, such as $HgCl_2$ and thereafter heating the sample again and observing the temperature at which the mercury is evolved. It is clear that a calibration for commonly occurring mercury salts can be prepared by the technique discussed as well as by other techniques known to those skilled in the art. For purposes of the present invention, it is necessary that the decomposition temperatures for the mercury sulfide be determined with the other mercury being allowed to thermally decompose and evolve without particular concern as to the form of the mercury in the soil. The ratio of the mercury sulfide to total mercury is then readily calculated.

The higher ratios of mercury sulfide to the total mercury indicate the presence of subterranean sulfide mineral ore deposits. While applicant does not wish to be bound by any theory, it is postulated that over the millions of years, the sulfide mineral ore deposits release sulfur slowly, thus providing reactive sulfides which move upwardly through the soil and react with the mercury in the soil, thus increasing the ratio of mercury sulfide to the total mercury present in the soil in areas over sulfide mineral ore deposits. Obviously, in some instances, the higher ratios may occur in only a portion of the area overlying sulfide mineral ore deposits, since the reactive sulfides would tend to move upwardly through the more porous earth formations and the like.

It is recognized that in many instances, the total amount of mercury contained in the soil samples will be quite low, and it is pointed out that the total amount of mercury is of no particular concern. The information of interest in the analysis of the soil is the ratio of the mercury sulfide to total mercury present in the soil. It is desirable that efforts be made to avoid the collection of non-representative samples in areas which have been sprayed for crop treatment and the like by taking samples from a suitable depth in the soil.

It is pointed out the foregoing description of preferred embodiments is illustrative rather than limiting in nature and that numerous variations and modifications are possible within the scope of the present invention. Such modifications and variations may appear obvious or desirable to those skilled in the art upon a review of the foregoing description of preferred embodiments and the following examples.

EXAMPLE 1

Numerous samples were collected in a 6-foot diameter circle. The ratio of HgS to the total mercury was determined on each sample. The data are shown below in Table I.

TABLE I

| Hole No. | Depth (Inches) | Parts Per Billion Total Hg | Ratio HgS/Total Hg |
|---|---|---|---|
| 1 | 3–5 | 12.9 | .122 |
| 3 | 2–3 | 16.2 | .105 |
| 5 | 2–3 | 18.2 | .099 |
| 9 | 2–3 | 14.2 | .108 |
| 13 | 5–7 | 24.9 | .100 |
| 14 | 5–7 | 27.8 | 104 |
| 15 | 5–7 | 23.9 | .114 |
| 20 | 5–7 | 17.3 | .105 |
| 21 | 5–7 | 21.1 | .116 |
| 31 | 11–13 | 14.0 | .102 |
| Mean | | 19.05 | .1075 |

It is clear that the ratio of HgS to the total mercury present in the sample remains relatively constant at the various depths, although it will be noted that the total mercury varies significantly. In further tests, it was determined that the variation in the ratio of HgS to total mercury present is very slightly greater than the experimental error in the test method used.

The soil analyses were accomplished by heating the soil samples and measuring the evolved mercury at given temperatures as discussed hereinbefore.

EXAMPLE 2

A plurality of soil samples were collected over an area known to include a sulfide mineral ore deposit, more particularly a copper sulfide ore deposit. Areas of high HgS to total mercury ratios were discovered over the ore deposit. It was clearly indicated that a sulfide mineral ore deposit was present in the area considered.

EXAMPLE 3

A second area known to include a copper sulfide deposit was tested in a similar manner. Two of the three areas having the highest ratios occurred over the ore body, and at present, no other tests have been run to confirm the presence of sulfide mineral ore deposits in the other area having high ratios.

The foregoing examples clearly show that the method of the present invention is effective in determining the location of sulfide mineral ore deposits in a given area of interest.

Having thus described the invention, I claim:

1. A method for locating subterranean sulfide mineral ore deposits, said method consisting essentially of:
    a. analyzing the soil at a plurality of locations in an area of interest to determine a ratio between mercury present in the soil as mercury sulfides and the total mercury present in the soil at said locations; and,
    b. comparing said ratios to determine the location of sulfide mineral ore deposits in said area of interest.

2. The method of claim 1 wherein said mineral ore deposits are ores of metals selected from the group consisting of copper, zinc, lead, silver, cadmium, mercury, and mixtures thereof.

3. The method of claim 1 wherein said soil is analyzed by:
    c. collecting representative samples at each of said locations; and,
    d. analyzing said samples to determine the ratio between said mercury sulfides and said total mercury in each of said samples.

4. The method of claim 1 wherein said mercury sulfides are selected from the group consisting of HgS, $Hg_2S$, and mixtures thereof.

5. The method of claim 4 wherein said mercury sulfides are HgS.

* * * * *